United States Patent [19]
Forlani et al.

[11] Patent Number: 4,814,542
[45] Date of Patent: Mar. 21, 1989

[54] OLEFIN BOND ISOMERIZATION PROCESS

[75] Inventors: Orfeo Forlani, Milan; Francesco Ancillotti; Bruno Notari, both of S.Donato Milanese, all of Italy

[73] Assignee: Snamprogetti, S.p.A., Milan, Italy

[21] Appl. No.: 224,359

[22] Filed: Jul. 26, 1988

Related U.S. Application Data

[63] Continuation of Ser. No. 120,972, Nov. 16, 1987, abandoned, which is a continuation of Ser. No. 644,660, Aug. 27, 1984, abandoned, which is a continuation of Ser. No. 494,668, May 16, 1983, abandoned.

[51] Int. Cl.$^4$ ............................................. C07C 5/25
[52] U.S. Cl. .................................... 585/666; 585/664
[58] Field of Search ................................ 585/664, 666

[56] References Cited

U.S. PATENT DOCUMENTS 3,467,727  9/1969  Kahn ..................................... 585/664
3,479,415 11/1969  Shule .................................... 585/666
3,864,424  2/1975  Brennan et al. ....................... 585/666
4,217,244  8/1980  Montgomery ......................... 585/666
4,229,610 10/1980  Myers et al. .......................... 585/664

FOREIGN PATENT DOCUMENTS 2121430 12/1983  United Kingdom ................ 585/666

Primary Examiner—Asok Pal
Attorney, Agent, or Firm—Hedman, Gibson, Costigan & Hoare

[57] ABSTRACT

A process for olefin bond isomerization by means of a gamma alumina-based catalyst containing $SiO_2$ and oxides of a metal chosen from those of Group II A and/or VIII and/or III B and/or Lanthanides, with particular molar ratios between the various oxides. The catalyst is thermally stable, and in the conversion of butene-2 to butene-1 enables butene-1 to be obtained with an isobutene content below the allowable limits for butene-1 grade polymerization.

12 Claims, No Drawings

OLEFIN BOND ISOMERIZATION PROCESS

This is a continuation of U.S. application Ser. No. 120,972, filed Nov. 16, 1987, which is a continuation of Ser. No. 644,660, filed Aug. 27, 1984, which is a continuation of Ser. No. 494,668, filed May 16, 1983, now all abandoned.

This invention relates to an olefin bond isomerisation process.

More particularly, the invention relates to a process for the isomerisation of butene-2 to butene-1. Certain olefin bond isomerisation processes are known, and reference can be made in this respect to U.S. Pat. Nos. 3,475,511 and 4,229,610.

The processes of the known art have not however found any industrial application, in that the catalysts used in them have difficulty in undergoing the necessary regeneration due to the formation of carbon residues during operation.

Regeneration must be effected at high temperature, and known catalysts lose their activity characteristics during this, mainly because of the collapse of the surface area.

The Journal of Catalysis (49, 285 (1977)) states that butene bond isomerisation can be effected in the presence of a catalyst constituted by lanthanum oxides.

The tests reported therein show however that the reaction is very slow, with the result that very low space velocities are necessary in order to attain acceptable conversion, and in addition the catalyst is sensitive even to traces of moisture, so that it has to be regenerated in a very complicated and costly manner.

It has been surprisingly found that the drawbacks of the known art can be obviated by using for the olefin bond isomerisation reaction a catalyst constituted in its final form by $Al_2O_3$, $SiO_2$ and an oxide of one or more bivalent or trivalent metals chosen from those of Group II A, particularly calcium, barium or strontium, and/or Group VIII, particularly iron, and/or Group III B, particularly lanthanum or lanthanides.

The process according to the present invention consists of bringing the olefin to be isomerised into contact at a temperature of between 350° C. and 550° C., preferably between 450° C. and 500° C., at a pressure of between 0.1 and 10 ata, preferably between 0.5 and 3 ata, with a gamma alumina-based catalyst corresponding to the general molar formula $$aAl_2O_3 \cdot bSiO_2 \cdot cMe_xO_y$$

where $Me_xO_y$ is the oxide of the bivalent or trivalent metal or metals chosen as heretofore stated, and a, b and c are the number of moles of $Al_2O_3$, $SiO_2$ and $Me_xO_y$ respectively, b and c being related by the relationship $c = mb + B$, where B has a value greater than or equal to 0.01, and b has a value between 0 and 0.300, preferably between 0.020 and 0.250, the ratio $(b+c)/a$ being between 0,01 and 9.0, and m being a number between 0.7 and 0.1.

In the specific case of lanthanum, it has been found that the optimum relationship between the lanthanum oxide and silica is as follows:

moles $La_2O_3 \geqq 0.257 \times$ moles $SiO_2 + 0.014$ whereas in the case of calcium, the optimum relationship between the calcium oxide and silica is as follows:

moles $CaO \geqq 0.500 \times$ moles $SiO_2 + 0.030$

In the case of barium the optimum relationship between the barium oxide and silica is as follows:

moles $BaO \geqq 0.500 \times$ moles $SiO_2 + 0.020$

In the case of iron the optimum relationship between the ferric oxide and silica is as follows:

moles $Fe_2O_3 \geqq 0.29 \times$ moles $SiO_2 + 0.018$

According to the process of the present invention, the weight hourly space velocity (WHSV) of the olefin is between 2 and 20 $h^{-1}$, and preferably 4 and 8 $h^{-1}$. Regeneration is effected in the conventional manner by heating in a controlled oxygen atmosphere to a temperature of between 470° and 600° C.

The catalyst for use according to the invention is prepared in two stages:

(a) preparation of gamma alumina stabilised by silica; the stabilisation is carried out by the methods described in U.S. Pat. Nos. Re. 30668, 4,013,590 and 4,015,589. If silica is not used, then normal gamma alumina is utilised;

(b) impregnation of the alumina stabilised as stated under (a) or of the gamma alumina, with salts of bivalent or trivalent metals, preferably nitrates or acetates, followed by thermal treatment at a temperature of between 350° and 550° C.

It should be noted that the process according to the present invention not only enables the aforesaid regeneration drawbacks to be overcome, but also enables the level of isobutene produced when converting butene-2 to butene-1 to be maintained within the maximum allowable limits for the direct use of butene-1 in polymerisation reactions, ie. without having to purify the butene-1.

Some examples are given hereinafter in order to better illustrate the invention, but these are not to be taken as limiting thereof.

EXAMPLE 1

20 g of gamma alumina (surface area 200 m²/g) are impregnated with 15 cc of an aqueous solution containing 1.8 g of lanthanum nitrate. It is dried and calcined at 500° C. for 4 hours. A material is obtained comprising 3.5% by weight of $La_2O_3$ on alumina.

The catalyst obtained in this manner is placed in a flow reactor, in which the trans butene-2 isomerisation reaction is carried out. Table 1 gives the data relative to the test carried out, and the value of the surface areas of the materials concerned, after thermal treatment for 24 hours to 1000° C.

EXAMPLE 2

Following the procedure of Example 1, 20 g of alumina are impregnated with 15 cc of an aqueous solution containing 2.57 g of lanthanum nitrate.

A catalyst is obtained containing 5% by weight of $La_2O_3$ on alumina.

EXAMPLE 3

Following the procedure of Example 1, a catalyst is prepared containing 7.5% by weight of $La_2O_3$ on alumina.

EXAMPLE 4

Following the procedure of Example 1, a catalyst is prepared containing 10.0% by weight of $La_2O_3$ on alumina.

EXAMPLE 5

20 g of gamma alumina (S.A.a 200 m²/g) are treated with 15 cc of an alcohol solution containing 0.75 g of Dynasil A 40 (40% ethyl orthosilicate solution).

The mixture is allowed to react at 50° C., it is then drained off and treated with steam in order to hydrolyse the silanol groups. It is dried and calcined at 500° C. for 4 hours.

The material thus obtained, containing 1.5% of $SiO_2$, is impregnated with 2.57 g of lanthanum nitrate, as described in Example 2.

A material is obtained constituted by gamma alumina stabilised by 1.5% of $SiO_2$, and containing 5% of $La_2O_3$. This catalyst is loaded into a reactor, in which the isomerisation of trans butene-2 is carried out.

Table 2 gives the data relative to the tests carried out, and the value of the surface areas of the materials concerned, after thermal treatment for 24 hours at 1000° C.

EXAMPLE 6

20 g of silicified alumina, prepared as described in Example 5, are impregnated with an aqueous lanthanum nitrate solution by the procedure described in Example 3. A material is obtained consisting of alumina and 1.5% $SiO_2$ plus 7.5% $La_2O_3$.

EXAMPLE 7

A catalyst is prepared in the manner heretofore described, constituted by alumina, stabilised by 1.5% $SiO_2$ and modified by 10% of $La_2O_3$.

EXAMPLE 8

20 g of alumina are impregnated, by the procedure of Example 5, with an alcohol solution of ethyl orthosilicate to give a material which, after treatment with steam and calcining, contains 3.8% of $SiO_2$.

This material is then impregnated with the necessary quantity of lanthanum nitrate solution to give 5.0% of $La_2O_3$. A catalyst is obtained in this maner containing 3.8% $SiO_2$ and 5.0% $La_2O_3$ on alumina.

Catalytic tests are carried out with this material.

EXAMPLE 9

A catalyst of composition 3.8% $SiO_2$ and 7.5% $La_2O_3$ on alumina is prepared in the manner described in Example 8.

EXAMPLE 10

A catalyst of composition 3.8% $SiO_2$ and 10.0% $La_2O_3$ on alumina is prepared in the manner described in Example 8.

EXAMPLE 11

A catalyst of composition 8% $SiO_2$ and 5% $La_2O_3$ on alumina is prepared in the aforesaid manner.

EXAMPLE 12

A catalyst of composition 8% $SiO_2$ and 7.5% $La_2O_3$ on alumina is prepared in the aforesaid manner.

EXAMPLE 13

A catalyst of composition 8% $SiO_2$ and 10.0% $La_2O_3$ on alumina is prepared in the aforesaid manner.

EXAMPLE 14

A catalyst of composition 8% $SiO_2$ and 15.0% $La_2O_3$ on alumina is prepared in the aforesaid manner.

EXAMPLE 15

Using the silicified alumina prepared as described in Example 8, a catalyst is prepared by impregnating said silicified alumina (3.8% $SiO_2$) with an aqueous solution of rare earth acetate, in a quantity such as to provide a final catalyst containing 10% of rare earth oxide.

The data given in Table 2 show the extent to which the behaviour of pure lanthanum and a mixture of rare earths is identical.

EXAMPLE 16

A catalyst of composition 1.5% $SiO_2$+2.5% CaO on alumina is prepared in the aforesaid manner. The calcium is introduced, analogously to the lanthanum, by using a calcium nitrate solution.

The data are given in Table 3.

EXAMPLE 17

A catalyst of composition 1.5% $SiO_2$+5.0% CaO on alumina is prepared.

EXAMPLE 18

A catalyst of composition 1.5% $SiO_2$+7.5% CaO on alumina is prepared.

EXAMPLE 19

A catalyst of composition 3.8% $SiO_2$+2.5% CaO on alumina is prepared.

EXAMPLE 20

A catalyst of composition 3.8% $SiO_2$+5.0% CaO on alumina is prepared.

EXAMPLE 21

A catalyst of composition 3.8% $SiO_2$+7.5% CaO on alumina is prepared.

EXAMPLE 22

A catalyst of composition 1.5% $SiO_2$+4.0% BaO on alumina is prepared in the aforesaid manner (the barium is introduced analogously to the calcium, by using a barium nitrate solution).

The data are given in Table 4.

EXAMPLE 23

A catalyst of composition 1.5% $SiO_2$+8.0% BaO on alumina is prepared.

EXAMPLE 24

A catalyst of composition 3.8% $SiO_2$+4.0% BaO on alumina is prepared in the aforesaid manner.

EXAMPLE 25

A catalyst of composition 3.8% $SiO_2$+8.0% BaO on alumina is prepared in the aforesaid manner.

EXAMPLE 26

A catalyst of composition 3.8% $SiO_2$+3.5% SrO on alumina is prepared in the aforesaid manner.

The results given in Table 4 show that strontium behaves in a manner analogous to calcium and barium.

EXAMPLE 27

A catalyst of composition 1.5% $SiO_2$ and 2.5% $Fe_2O_3$ (by weight) on alumina is prepared in the aforesaid manner. (The iron is introduced as an aqueous solution of iron nitrate). The data are given in Table 5.

EXAMPLE 28

A catalyst of composition 1.5% $SiO_2$ and 3.8% $Fe_2O_3$ by weight on gamma alumina is prepared in the aforesaid manner.

EXAMPLE 29

A catalyst of composition 1.5% $SiO_2$ and 5.0% $Fe_2O_3$ on gamma alumina is prepared in the aforesaid manner.

EXAMPLE 30

A catalyst of composition 3.8% $SiO_2$ and 2.5% $Fe_2O_3$ on gamma alumina is prepared in the aforesaid manner.

EXAMPLE 31

A catalyst of composition 3.8% $SiO_2$ and 3.8% $Fe_2O_3$ by weight is prepared in the aforesaid manner.

EXAMPLE 32

A catalyst of composition 3.8% $SiO_2$ and 5.0% $Fe_2O_3$ by weight is prepared in the aforesaid manner.

EXAMPLE 33

A catalyst of composition 5.0% $SiO_2$ and 2.5% $Fe_2O_3$ on gamma alumina is prepared in the aforesaid manner.

EXAMPLE 34

A catalyst of composition 5.0% $SiO_2$ and 3.8% $Fe_2O_3$ on gamma alumina is prepared in the aforesaid manner.

EXAMPLE 35

A catalyst of composition 5.0% $SiO_2$ and 5% $Fe_2O_3$ on gamma alumina is prepared in the aforesaid manner.

EXAMPLE 36

A catalyst of composition 5.0% $SiO_2$ and 7.5% $Fe_2O_3$ on gamma alumina is prepared in the aforesaid manner.

TABLE 1

Selective isomerisation of trans butene-2 to butene-1
Reaction conditions: T = 470° C.; P = 1 ata; WHSV = 6

| Catalyst | % $La_2O_3$ | Surface area (24 h, 1000° C.) $m^2/g$ | Isobutene content of reaction products (the linear butenes are always present in a quantity corresponding to thermodynamic equilibrium at the reaction temperature) |
|---|---|---|---|
| Ex 1 | 3.5 | 152 | 1300 p.p.m. |
| Ex 2 | 5.0 | 151 | 450 p.p.m. |
| Ex 3 | 7.5 | 120 | 350 p.p.m. |
| Ex 4 | 10.0 | 117 | 350 p.p.m. |

N.B. Example 1 clearly shows that on operating outside the range of the invention, butene-1 cannot be obtained with an isobutene content below the maximum allowable limit (0.1% by weight with respect to the butene-1)

TABLE 2

Isomerisation of trans butene-2 to butene-1
Reaction conditions: T = 470° C.; P = 1 ata; WHSV = 6

| Catalyst | % $La_2O_3$ | % $SiO_2$ | Surface area (24 h, 1000° C.) $m^2/g$ | Isobutene content of reaction products (the linear butenes are always present in the quantity corresponding to thermodynamic equilibrium at the reaction temperature) |
|---|---|---|---|---|
| Ex 5 | 5.0 | 1.5 | 154 | 990 p.p.m. |
| Ex 6 | 7.5 | 1.5 | 134 | 490 p.p.m. |
| Ex 7 | 10.0 | 1.5 | 113 | 140 p.p.m. |
| Ex 8 | 5.0 | 3.8 | 164 | 0.35% |
| Ex 9 | 7.5 | 3.8 | 163 | 0.145% |
| Ex 10 | 10.0 | 3.8 | 139 | 330 p.p.m. |
| Ex 11 | 5.0 | 8.0 | 188 | 0.7% |
| Ex 12 | 7.5 | 8.0 | 170 | 1.4% |
| Ex 13 | 10.0 | 8.0 | 155 | 1500 p.p.m. |
| Ex 14 | 15.0 | 8.0 | 145 | 200 p.p.m. |
| Ex 15 | 10.0 | 3.8 | 143 | 380 p.p.m. |
| (as rare earth oxides) | | | | |

For Examples 5, 8, 9, 11, 12, 13, see note relative to Example 1.

TABLE 3

Isomerisation of trans butene-2 to butene-1
Reaction conditions: T = 470° C.; P = 1 ata; WHSV = 6

| Catalyst | % CaO | % SiO2 | Surface area (24 h, 1000° C.) $m^2/g$ | Isobutene content of reaction products (the linear butenes are always present in a quantity corresponding to thermodynamic equilibrium at the reaction temperature) |
|---|---|---|---|---|
| Ex 16 | 2.5 | 1.5 | 183 | 150 p.p.m. |
| Ex 17 | 5.0 | 1.5 | 147 | 270 p.p.m. |
| Ex 18 | 7.5 | 1.5 | 136 | 300 p.p.m. |
| Ex 19 | 2.5 | 3.8 | 185 | 450 p.p.m. |
| Ex 20 | 5.0 | 3.8 | 155 | 250 p.p.m. |
| Ex 21 | 7.5 | 3.8 | 150 | 150 p.p.m. |

All catalysts of Examples 1 to 20 were subjected to ageing tests consisting of 40 reaction cycles (332 hours in total) and 40 regeneration cycles (152 hours in total), without showing loss of activity. Regeneration was effected at a temperature of 540° C.

TABLE 4

Isomerisation of trans butene-2 to butene-1
Reaction conditions: T = 470° C.; P = 1 ata; WHSV = 6

| Catalyst | % BaO (by weight) | % SiO₂ (by weight) | Surface area (24 h, 1000° C.) $m^2/g$ | Isobutene content of reaction products (the linear butenes are always present in a quantity corresponding to thermodynamic equilibrium at the reaction temperature) |
|---|---|---|---|---|
| Ex 22 | 4.0 | 1.5 | 192 | 260 p.p.m. |
| Ex 23 | 8.0 | 1.5 | 151 | 130 p.p.m. |
| Ex 24 | 4.0 | 3.8 | 189 | 470 p.p.m. |
| Ex 25 | 8.0 | 3.8 | 154 | 230 p.p.m. |
| Ex 26 | 3.5% (SrO) | 3.8 | 185 | 280 p.p.m. |

TABLE 5

Isomerisation of trans butene-2 to butene-1
Reaction conditions: T = 470° C.; P = 1 ata; WHSV = 6

| Catalyst | % Fe₂O₃ (by weight) | % SiO₂ (by weight) | Surface area (24 h, 1000° C.) $m^2/g$ | Isobutene content of reaction products (the linear butenes are always present in a quantity corresponding to thermodynamic equilibrium at the reaction temperature). |
|---|---|---|---|---|
| Ex 27 | 2.5 | 1.5 | 161 | 1100 p.p.m. |
| Ex 28 | 3.8 | 1.5 | 129 | 430 p.p.m. |
| Ex 29 | 5.0 | 1.5 | 130 | 200 p.p.m. |
| Ex 30 | 2.5 | 3.8 | 158 | 0.41% |
| Ex 31 | 3.8 | 3.8 | 165 | 0.12% |
| Ex 32 | 5.0 | 3.8 | 141 | 420 p.p.m. |
| Ex 33 | 2.5 | 5.0 | 190 | 1.2% |
| Ex 34 | 3.8 | 5.0 | 170 | 0.9% |
| Ex 35 | 5.0 | 5.0 | 155 | 1800 p.p.m. |
| Ex 36 | 7.5 | 5.0 | 150 | 350 p.p.m. |

For Examples 27, 30, 31, 33, 34, 35, see note relative to Example 1.

We claim:

1. A process for olefin bond isomerisation in the presence of a gamma alumina based catalyst, said process comprising the isomerisation of butene-2 in the presence of a catalyst which consists essentially of a mixtur of gamma alumina and lanthanum oxide wherein the content of La₂O₃ is from 5 to 10% by weight; the alumina content is from 90–95% by weight and the surface area is from 151–117 square meters per gram.

2. A process for olefin bond isomerisation in the presence of gamma alumina, said process comprising the isomerisation of butene-2 in the presence of a catalyst which consists essentially of a mixture of gamma alumina, silica and lanthanum oxides wherein the gamma alumina is from 77 to 91% by weight; the silica is from 1.5 to 8% by weight and the lanthanum oxide is from 7.5 to 15% by weight and the catalyst has a surface area is from 113 to 145 square meters per gram.

3. A process for olefin bond isomerisation in the presence of a gamma alumina catalyst, said process comprising the isomerisation of butene-2 in the presence of a catalyst which consists essentially of gamma alumina, silica and calcium wherein the content of gamma alumina is from 88.7 to 96% by weight; the silica content is from 1.5 to 3.8% by weight of silica and from 2.5 to 7.5% calcium oxide and the catalyst has a surface area of 136 to 185 square meters.

4. A process for olefin bond isomerisation in the presence of a gamma alumina catalyst, said process comprising the isomerisation of butene-2 in the presence of a catalyst which consists essentially of gamma alumina, silica and barium oxide wherein the content of gamma alumina is from 88.2 to 94.5% by weight; the silica is from 1.5 to 3.8%; the barium oxide is from 4 to 8% by weight; and the catalyst has a surface area of from 151 to 192 square meters per gram.

5. A process for olefin bond isomerisation in the presence of a gamma alumina catalyst, said process comprising the isomerisation of butene-2 in the presence of a catalyst which consists essentially of gamma alumina, silica and ferric oxide, wherein the content of gamma alumina is from 87.5 to 94.7% by weight, the silica is from 1.5 to 5% by weight; the ferric oxide is from 3.8 to 7.5% by weight and the catalyst has a surface area of from 129 to 150 square meters per gram.

6. A process as defined in claim 1 wherein the catalyst consists essentially of 5% $La_2O_3$ by weight; and 95% alumina by weight and has a surface area of 151 square metters.

7. A process as defined in claim 1 wherein the catalyst consists essentially of 7.5% $La_2O_3$ by weight and 92.5% alumina by weight and has a surface area of 120 square meters.

8. A process as defined in claim 1 wherein the catalyst consists essentially of 10% $La_2O_3$ by weight and 90% alumina by weight and has a surface area of 117 square meters.

9. A process as defined in claim 2 wherein the catalyst consists essentially of 7.5% $La_2O_3$ by weight 1.5% silica by weight; and 91% alumina by weight and has a surface area of 134 square meters.

10. A process as defined in claim 2 wherein the catalyst consists essentially of 10% $La_2O_3$ by weight; 1.5% silica by weight; 88.5% by alumina by weight and has a surface area of 139 square meters.

11. A process as defined in claim 2 wherein the catalyst consists essentially of 15% $La_2O_3$ by weight; 8.0% silica by weight; and 77% alumina by weight and has a surface area of 145 square meters.

12. A process as defined in claims 1, 2, 3, 4 or 5, wherein the product is butene-1 has an isobutene content below the allowable limits for butene-1 polymerization.

* * * * *